US00PP32019P3

(12) United States Plant Patent
Olesen et al.

(10) Patent No.: US PP32,019 P3
(45) Date of Patent: Jul. 28, 2020

(54) ***CLEMATIS* PLANT NAMED 'EVIPO065'**

(50) Latin Name: *Clematis cartmanii*
Varietal Denomination: Evipo065

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,903

(22) Filed: Sep. 10, 2018

(65) Prior Publication Data

US 2020/0084939 P1 Mar. 12, 2020

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
See application file for complete search history.

(56) References Cited

PUBLICATIONS

UPOV hit on *Clematis* plant named'Evipo065', QZ PBR 20172264, filed Sep. 19, 2017.*
http://www.poulsenroser.com/assortment/clematis-collections/boulevard/xiu.aspx, downloaded Jun. 20, 2019.*

* cited by examiner

*Primary Examiner* — Anne Marie Grunberg

(57) ABSTRACT

A new *Clematis* plant with a compact growth habit, profuse, white flowers, and early spring flowering. The variety successfully propagates from softwood cuttings and is suitable for cultivation in commercial nursery culture. This new and distinct variety has shown to be uniform and stable in the resulting generations from asexual propagation from vegetative cuttings.

3 Drawing Sheets

Botanical classification:
Genus: *Clematis.*
Species: *cartmanii.*
Variety denomination: 'Evipo065'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 1995 and the resulting seeds were planted the following winter in a controlled environment in Guernsey, Channel Islands, United Kingdom. The new variety named 'Evipo065' originated as a single seedling from the stated cross.

The new *clematis* plant may be distinguished from its female seed parent and male pollen parent by the following characteristics. The new variety has green white reproductive flower parts while the seed parent variety has yellow white reproductive flower parts. The male pollen parent variety grows flowers at 30 cm from the base of the plant, while the new variety is 15 cm from the base of the plant to the flowering portion.

The objective of the hybridization of this *clematis* plant was to create a new and distinct variety for nursery culture with unique qualities such as:

1. Uniform and abundant white flowers;

2. Vigorous and compact growth, making the variety suitable for container culture; and
3. Improved disease resistance; and
4. Very early flowering.

This combination of qualities was lacking in *clematis* plants that were in commercial cultivation and the qualities have been substantially achieved in the new variety.

'Evipo065' was selected by Mogens N. Olesen and Raymond J. Evison in their *clematis* development program in the Channel Islands, United Kingdom in 1996. Asexual reproduction of 'Evipo065' by means of vegetative stem cuttings and was first performed by Mogens N. Olesen and Raymond J. Evison in their nursery location in St. Sampean, Guernsey, Channel Islands during the summer of 1996. This initial and subsequent asexual propagations have demonstrated that the characteristics of 'Evipo065' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo065'.

Specifically illustrated in FIG. 1 of the drawings is a branch with leaves.

DETAILED DESCRIPTION OF THE VARIETY

Figure 1:
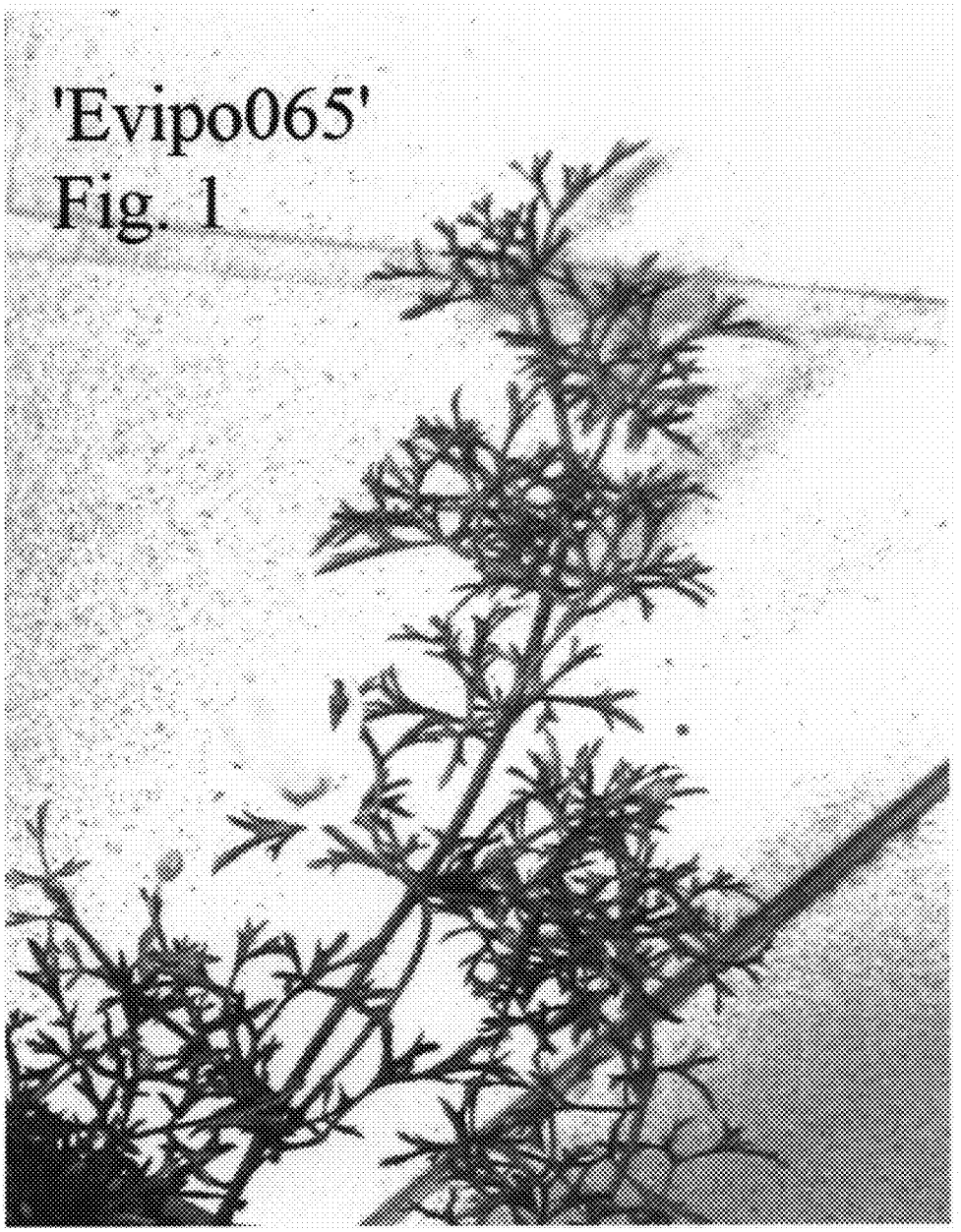
Figure 2:
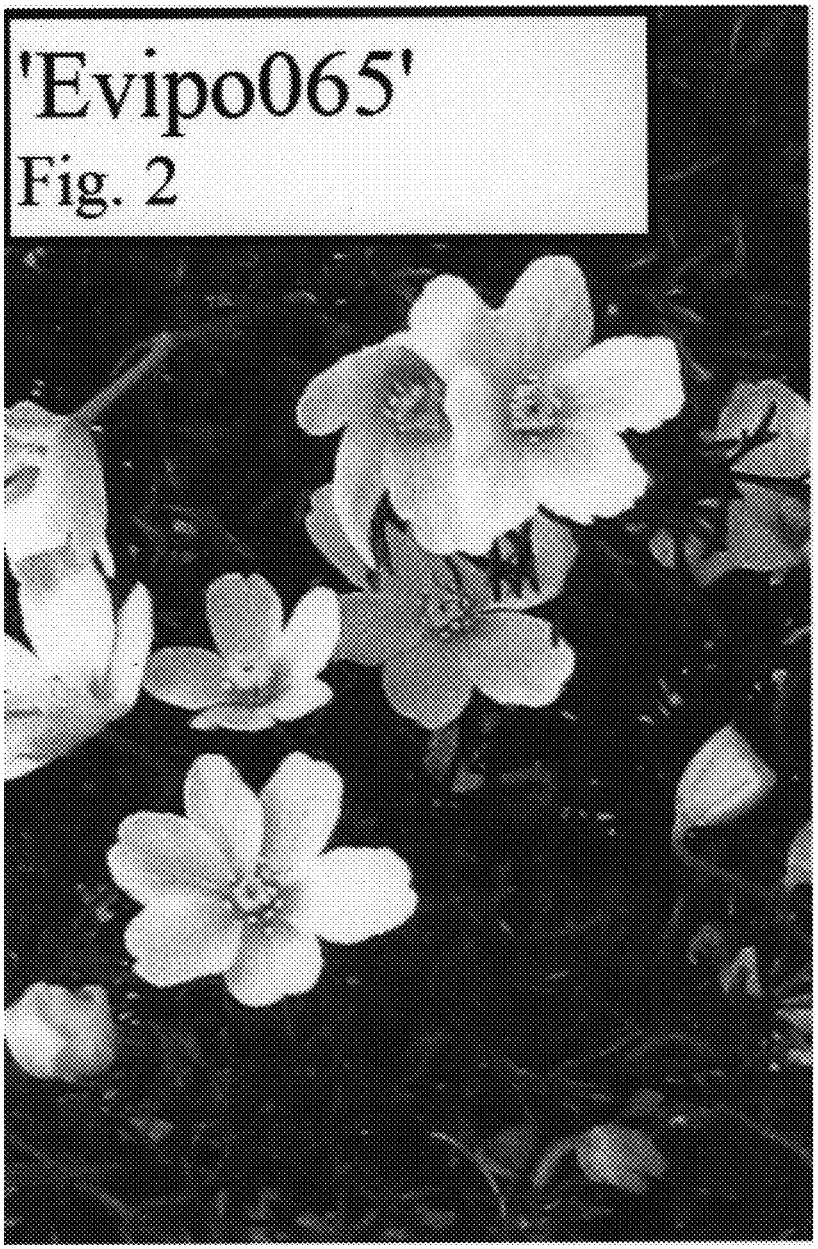
FIG. 2 shows open flowers.
Figure 3:
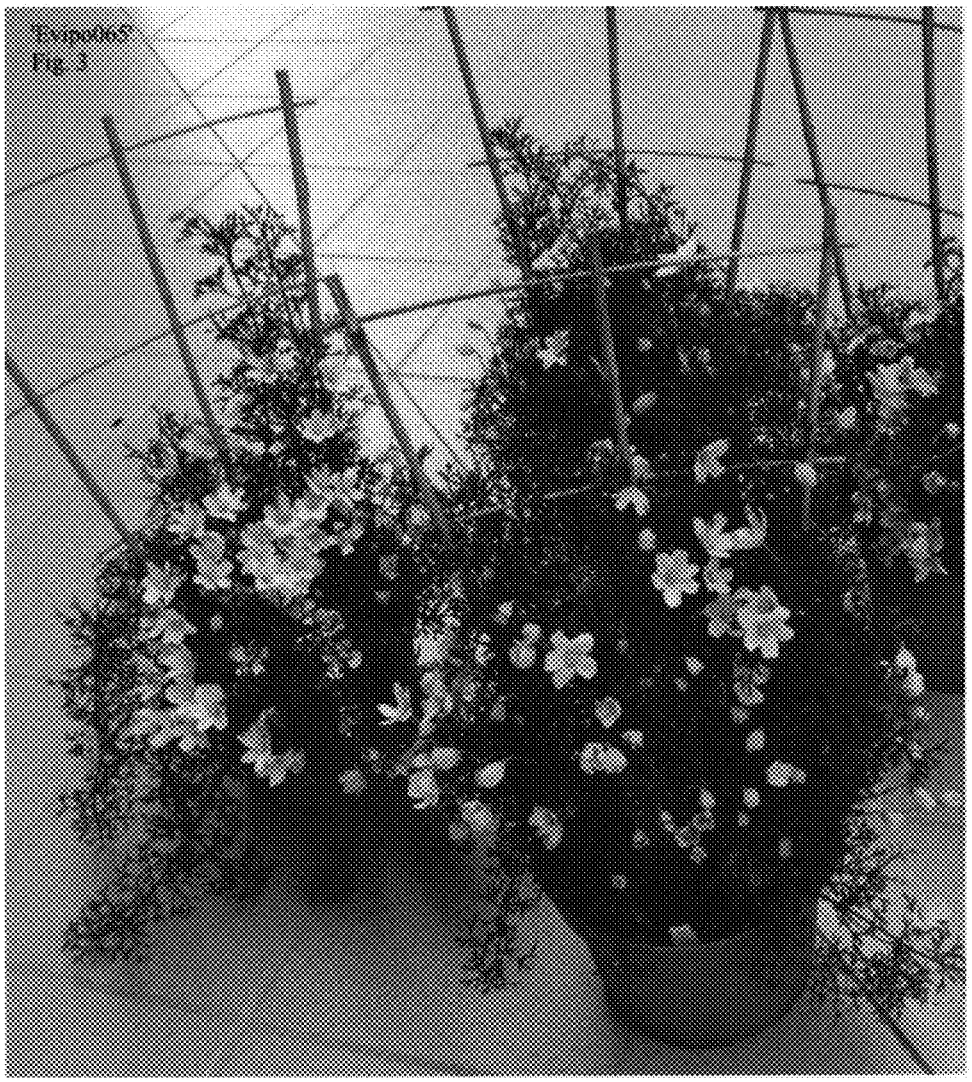
FIG. 3 shows two specimens of 'Evipo065' flowering in containers. Illustrated plants are 2 years of age.

The following is a detailed description of 'Evipo065', as observed in its growth throughout the flowering period in Denmark. Observed plants were cultivated for a period of 24 months in 24 cm containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo066' described and illustrated in U.S. Plant Pat. No. 27,283 are compared to 'Evipo065' in Chart 1.

CHART 1

| | 'Evipo065' | 'Evipo066' |
|---|---|---|
| Flower diameter | 55 mm | 60 mm |
| Tepal margin | undulated, with cleft at apex | entire, no undulations |

Flower and Flower Bud

Blooming habit: The natural flowering period is early April to May.

Pedicel:
- *Surface texture.*—Smooth.
- *Length.*—35-45 mm.
- *Color.*—Yellow-Green Group 146D.
- *Strength.*—Moderately strong.

Receptacle:
- *Surface texture.*—Smooth.
- *Shape.*—Funnel.
- *Size.*—2 mm (h)×2 mm (w).
- *Color.*—Yellow-Green Group 146D.

Flower arrangement:
- *Location on vine.*—Old growth.
- *Borne.*—Flowers develop from nodes along the stem.

Flower bloom:
- *Size.*—On average, flowers are 55 mm in diameter and 10 mm in depth.
- *Profile.*—Open flowers are convex.
- *Fragrance.*—None.
- *Lasting quality.*—Flowers normally remain 10 days on the plant.

Tepals:
- *Tepal color.*—The upper surface and lower is Green White Group 157B.
- *Tepal overlap.*—Strong.
- *Quantity.*—Normally 6 tepals.
- *Size.*—27 mm in length by 10 mm wide.
- *Shape.*—Individual tepal shape is lanceolate The tepal apex is rounded with a cleft. The base is acute.
- *Apex recurvature.*—None.
- *Tepal cross section.*—Flat.
- *Margins.*—Entire and undulated at the apex.
- *Persistence.*—Tepals drop away cleanly.

Reproductive organs:
- *Pollen.*—None observed.
- *Anthers.*—Size: About 2 mm in length. Color: Green-White Group 157C. Quantity: On average, 35.
- *Filaments.*—Color: Yellow-Green Group 150D. Length: 10 mm.
- *Pistils.*—None observed.

Seed head characteristics: Not observed.

Plant

Plant form: Bushy.

Plant growth: Moderately vigorous.

Size: Seasons growth attains 55 cm in height. Average spread is 60 cm.

Stems:
- *Color.*—Yellow-Green Group 146B. Mature stems are Brown Group 200B.
- *Internodes.*—On average, 60 mm between nodes.
- *Length.*—Normally 15 cm from the base of the plant to the flowering portion of the stem.
- *Diameter.*—Normally 2 to 4 mm.
- *Texture.*—Mature stems are generally smooth.

Plant foliage:
- *Leaf characteristics.*—Evergreen.
- *Arrangement.*—Biternate, opposite.
- *Leaf size.*—Compound leaves are about 65 mm (l)×60 mm (w). Leaflets are normally 25 mm (l)×8 mm (w).
- *Abundance.*—On average 2 leaves per 10 cm of stem.
- *Leaf color.*—Juvenile upper Yellow-Green Group 146A. Juvenile lower Yellow-Green Group 146A. Mature upper Yellow-Green Group 147A with intonations of Greyed-Purple Group N186B. Mature lower Yellow-Green Group 146A.
- *Stipules.*—Absent.
- *Petioles.*—Size: Normally 28 mm in length by 1 to 2 mm diameter. Texture: Smooth. Color: Yellow-Green Group 147A.
- *Petioloule.*—Size: Normally 18 mm in length by 1 to 2 mm diameter. Texture: Smooth. Color: Yellow-Green Group 147A.
- *Leaflet shape.*—Linear, digitate. The base and apex are acute.
- *Margin.*—With 3 to 5 lobes.
- *Surface.*—The upper and lower surfaces are smooth.
- *Thickness.*—Thick.
- *Glossiness.*—Glossy.

Disease resistance: Subject to any disease that normally attacks the species.

Cold hardiness: Trials to date show the variety is hardy to −10° C.

Heat tolerance: The variety has been found to be suitable for climate conditions found in the American Horticulture Society heat zone 7.

We claim:

1. A new and distinct variety of *clematis* plant named 'Evipo065', substantially as described and illustrated, due to its abundant white flowers with good keepability, attractive long lasting foliage and compact growth, suitability for production from softwood cuttings in pots, durable flowers and foliage which make the variety suitable for distribution in the floral industry.

* * * * *

'Evipo065'

'Evipo065'

Evapelto5